United States Patent [19]

Rowlands et al.

[11] Patent Number: 6,043,078

[45] Date of Patent: Mar. 28, 2000

[54] METHOD FOR THE REDUCTION OF BIOLOGICAL GROWTH IN SOLUTION

[75] Inventors: Anne G. Rowlands, Honeoye Falls; Mark S. Fornalik, Rochester, both of N.Y.

[73] Assignee: Eastman Kodak Company, Rochester, N.Y.

[21] Appl. No.: 09/182,917

[22] Filed: Oct. 30, 1998

[51] Int. Cl.$^7$ .................................................. A61K 38/47
[52] U.S. Cl. ........................ 435/273; 424/94.6; 424/94.61
[58] Field of Search ................................ 424/94.6, 94.61; 435/273

[56] References Cited

FOREIGN PATENT DOCUMENTS

| 774504 | 5/1997 | European Pat. Off. . |
|---|---|---|
| 4343128 | 6/1995 | Germany . |
| 9622252 | 7/1996 | WIPO . |

*Primary Examiner*—Jean C. Witz
*Attorney, Agent, or Firm*—Carl F. Ruoff; Doreen M. Wells

[57] ABSTRACT

The present invention is a process for reducing biological growth in aqueous solutions. An aqueous solution is provided. An amylase solution is added to the aqueous solution to provide an amylase concentration of greater than 1 unit/ml enzyme activity thereby reducing biological growth in the aqueous solution.

4 Claims, No Drawings

METHOD FOR THE REDUCTION OF BIOLOGICAL GROWTH IN SOLUTION

CROSS REFERENCE TO RELATED APPLICATIONS

This application relates to commonly assigned copending application Ser. No., 09/183149 (Docket 78,452) filed simultaneously herewith incorporated by reference herein. This application relates to commonly assigned copending application Ser. No., 09/182936 (Docket 78,453), filed simultaneously herewith incorporated by reference herein.

FIELD OF THE INVENTION

The present invention relates to control of biological growth in aqueous solutions and more particularly to a method of controlling biological growth through the use of enzymes.

BACKGROUND OF THE INVENTION

Control of biological growth in solution is of critical interest to a number of industries. In the food industry, biological contamination and growth results in spoilage waste. In the photographic industry biological contamination and growth can also result in waste through spoilage of gelatin, emulsions, dispersions, photochemical solutions or melts. Additives to preserve solutions and prevent biological growth are numerous. The application of interest influences the choice of biogrowth inhibitor; biostat or biocide, and is further influenced by such issues as solubility, toxicity and possible detremental product effects. Biocides such as quaternary ammonium salts, carbamates and gluteraldehyde have been used but they have toxicity problems.

An object of the present invention is to reduce biological growth in aqueous solutions.

SUMMARY OF THE INVENTION

The present invention is a process for reducing biological growth in aqueous solutions. An aqueous solution is provided. An amylase solution is added to the aqueous solution to provide an amylase concentration of greater than 1 unit/ml enzyme activity thereby reducing biological growth in the aqueous solution.

DETAILED DESCRIPTION OF THE INVENTION

The present invention is a process for reducing biological growth in solution. A solution is provided and added to an amylase at a concentration of at least 1 unit/ml enzyme activity, preferably 10 units/ml. Amylase activity is determined by the Ektachem DT60 Analyzer. The presence of amylase in the solution reduces the growth of bio-organisms in the resulting solution.

Amylases are a group of widely occurring hydrolases which cleave the alpha 1,4-glyosidic bonds in oligosaccharides and polysaccharides like starch, glycogen and dextrans. Commercially available amylases produced through fermentation technology typically also contain contaminating protease activity. In the present invention it is required that the amylases be free of protease activity. Methods for eliminating protease activity are described in U.S. Ser. No. 09/182,936 (Docket 78,453).

Due to the catalytic nature of amylase, the ability to reduce biogrowth is not stoichiometric. Amylases are also water soluble and effective over a wide range of pH.

Amylase effectiveness on reduction of biological growth was determined by providing, solutions incubated with amylase (protease free) for varied amounts of time at temperatures ranging from 40–55° C. Total bacterial colonies in treated and untreated solutions were determined by analytical filtration followed by visualization with a microbial specific dye. Numbers and sizes of bacterial colonies were quantified by a computer interfaced automated visual imaging system. Briefly, a solution was filtered through a 12 micron pore size polycarbonate filter, rinsed with water, stained with Methylene Blue and rinsed again with water. The resulting filter was dried and analyzed by an automated visual inspection system. Equipment used included a Wild Macroscope with RS-170 camera, Ludl 8"×8" X–Y stage, autofocus and color light box. Bacterial colonies measured ranged from 20 to greater than 110 microns in diameter. Numbers of bacterial colonies per a specified size range were reported per ml of solution.

The concentration of amylase required to reduce biological growth in solution is dependent on the amylase used and it's specific activity. The use of crude enzyme preparations can show an initial rise in biological growth followed by a sharp decline, presumably due to nutrients available in crude enzyme preparations. Thus, the purity of the amylase of choice will also effect the time course of reduction of biological growth.

Amylases

| | |
|---|---|
| Maxamyl L | Genencor International |
| Termamyl 12L Type L | Novo Nordisk |

To maintain protein integrity amylase solutions used must be free of protease activity. The commercial amylases named above were treated according to the method of U.S. Ser. No. 09/182936 (Docket 78,453) to reduce protease activity.

Amylase Activity:

Amylase activity was monitored using the amylase activity slide kit for the Ektachem DT60 Analyzer. This assay is based on the hydrolysis of dyed starch to smaller dyed saccharides. Intensity of color generation is proportional to amylase activity. Amylase activity is reported in units/L.

EXAMPLE 1

Reduction of Biological Growth in a Gelatin Solution by addition of Termamyl or Maxamyl.

1,565 Units of protease free Termamyl or 1,380 Units of protease free Maxamyl were added to 85 mls of 1% photographic gelatin and incubated at 40° C. for varying times. Bacterial content of the control gelatin solution and the amylase containing gelatin solutions were monitored by analytical filteration combined with methylene blue staining as described above. Reduction of biological growth in the amylase containing gelatin solutions is shown below.

| | Bacterial colonies >20 microns per ml | | |
|---|---|---|---|
| | Day 0 | Day 2 | Day 9 |
| Control: 1% gelatin solution | 248 | 54,057 | 109,221 |
| 1% gelatin solution + Maxamyl | 194 | 81,376 | 40,630 |
| 1% gelatin solution + | 346 | 186,607 | 70,078 |

-continued

| | Bacterial colonies >20 microns per ml | | |
|---|---|---|---|
| | Day 0 | Day 2 | Day 9 |
| Termamyl | | | |

At day two all the gelatin samples show a marked increase in biological growth. The addition of either amylase resulted in additional biological growth beyond the 1% gelatin control solution at Day 2. Presumibly, this is due to added nutrients present in the amylases themselves which are prepared from fermentation broths. By day 9 both maxamyl and termamyl have reduced the biological content of the gelatin solution as compared to the control gelatin solution. At Day 9 Maxamyl addition to the gelatin solution produced a 62.8% reduction in bacterial colonies and Termamyl addition to the gelatin solution produced a 33.8% reduction in bacterial colonies when compared to a control gelatin solution.

EXAMPLE 2

Reduction of Biological Growth in a photoprocessing solution by addition of Termamyl or Maxamyl.

1,910 Units of protease free Termamyl or 1,410 Units of protease free Maxamyl were added to 90 mls of used photodeveloper solution (E6 reversal bath) pH 11, and incubated at 40° C. for varying amounts of time. Bacterial content of the control photoprocessing solution and the amylase containing photoprocessing solutions were monitored by analytical filteration combined with methylene blue staining as described above. Reduction of biological growth in the amylase containing photoprocessing solutions is shown below.

| | Bacterial colonies >20 microns per ml | | |
|---|---|---|---|
| | Day 0 | Day 3 | Day 6 |
| Control: | 43.4 | 51 | 89.8 |

-continued

| | Bacterial colonies >20 microns per ml | | |
|---|---|---|---|
| | Day 0 | Day 3 | Day 6 |
| photoprocessing solution | | | |
| Photoprocessing solution + Maxamyl | 31 | 46.3 | 28.8 |
| Photoprocessing solution + Termamyl | 42.7 | 54 | 58 |

In this study no appreciable benefit was observed in biological growth inhibition at Day 2 by addition of either amylase to the photoprocessing solution. However, by Day 6 a marked reduction in biological growth was observed in the photoprocessing solutions containing amylases. Measurement of bacterial colonies at Day 6 resulted in a 67.8% reduction of bacterial colonies in the photoprocessing solution containing Maxamyl, and a 35.4% reduction of bacterial colonies in the photoprocessing solution containing Termamyl.

The invention has been described in detail with particular reference to certain preferred embodiments thereof, but it will be understood that variations and modifications can be effected within the spirit and scope of the invention.

What is claimed is:

1. A process for reducing biological growth comprising providing an aqueous solution selected from a gelatin solution, a photodeveloper solution and a photoprocessing solution; adding to the aqueous solution of gelatin an amylase solution to provide an amylase concentration of greater than 1 unit/ml enzyme activity thereby reducing biological growth in the aqueous solution.

2. The process of claim 1 wherein the amylase solution is free of protease activity.

3. The process of claim 1 wherein the amylase concentration is greater than 10 unit/ml enzyme activity.

4. The process of claim 1 wherein the aqueous solution is a gelatin solution.

* * * * *